United States Patent
Campbell

(10) Patent No.: US 7,333,857 B2
(45) Date of Patent: Feb. 19, 2008

(54) TREATMENT OF PAIN

(75) Inventor: James N. Campbell, Luthersville, MD (US)

(73) Assignee: Arcl, Inc., Lutherville, MD (US)

( * ) Notice: Subject to any disclaimer, the term of this patent is extended or adjusted under 35 U.S.C. 154(b) by 342 days.

(21) Appl. No.: 10/892,793

(22) Filed: Jul. 16, 2004

(65) Prior Publication Data

US 2005/0055065 A1  Mar. 10, 2005

Related U.S. Application Data

(60) Provisional application No. 60/488,857, filed on Jul. 18, 2003.

(51) Int. Cl.
*A61N 1/34* (2006.01)

(52) U.S. Cl. ............... 607/46; 607/47; 607/48; 607/72; 607/117

(58) Field of Classification Search ............ 607/46–48, 607/72, 117
See application file for complete search history.

(56) References Cited

U.S. PATENT DOCUMENTS

| | | | |
|---|---|---|---|
| 4,044,774 A | 8/1977 | Corbin et al. | |
| 5,012,810 A | 5/1991 | Strand et al. | |
| 5,501,703 A | 3/1996 | Holsheimer et al. | |
| 6,024,702 A | 2/2000 | Iversen | |
| 6,027,456 A | 2/2000 | Feler et al. | |
| 6,208,902 B1 | 3/2001 | Boveja | |
| 6,233,488 B1* | 5/2001 | Hess | 607/58 |
| 6,308,103 B1 | 10/2001 | Gielen | |
| 6,314,325 B1 | 11/2001 | Fitz | |
| 6,495,020 B1 | 12/2002 | Swanson | |
| 6,516,227 B1 | 2/2003 | Meadows et al. | |
| 2001/0031999 A1* | 10/2001 | Carter et al. | 607/69 |
| 2003/0028147 A1 | 2/2003 | Aves et al. | |
| 2003/0093134 A1 | 5/2003 | Bradley | |
| 2003/0120323 A1 | 6/2003 | Meadows et al. | |

FOREIGN PATENT DOCUMENTS

WO   WO 99/56818   11/1999

OTHER PUBLICATIONS

Barolat, "Spinal cord stimulation for chronic pain management," *Arch Med Res* 31: 258-262 (2000).

Beurrier, et al., "High-frequency stimulation produces a transient blockade of voltage-gated currents in subthalamic neurons," *J Neurophysiol* 85(4): 1351-1356 (2001).

Burcheil and Hsu, "Pain and spasticity after spinal cord injury," *Spine* 26(24S): S146-S160 (2001).

(Continued)

Primary Examiner—Carl Layno
Assistant Examiner—Deborah Malamud
(74) Attorney, Agent, or Firm—Pabst Patent Group LLP

(57) ABSTRACT

The method disclosed herein entails spinal cord stimulation via electrodes placed directly into the dorsal horn, dorsal column, spinothalamic tract, nucleus cuneatus, nucleus gracilis, spinal tract of V, or spinal nucleus of V (nucleus caudalis) depending on the source of pain. This "intramedullary" stimulation "jams" or otherwise prevents the pain signal from being transmitted. The method provides a means to stimulate the targeted area directly, creating a stable means of stimulating the desired area, and decreasing stimulation of other structures.

19 Claims, 3 Drawing Sheets

OTHER PUBLICATIONS

Chen, et al., "Nervous system reorganization following injury," *Neuroscience* 111: 761-773 (2002).

Christensen, et al., "Chronic central pain after spinal cord injury," *J Neurotrauma* 14: 517-537 (1997).

Denkers, et al., "Dorsal root entry zone lesioning used to treat central neuropathic pain in patients with traumatic spinal cord injury," *Spine* 27(7): E177-E184 (2002).

Eide, et. al., *J Neurol Neurosurg Psychiatry* 60: 411-415 (1996).

Falci, et al., Dorsal root entry zone microcoagulation for spinal cord injury-related central pain: operative intramedullary electrophysiological guidance and clinical outcome,: *J Neurosurg.* 97(2 Suppl): 193-200 (2002).

Holsheimer, et al., "Clinical evaluation of parethesia steering with a new system for spinal cord stimulation instrumentation assessment," *Neurosurg* 42(3): 541-547 (1998).

Hunt, et al., "Stimulation of the dorsal spinal cord for treatment of intractable pain: A preliminary report," *Surg Neurol* 4: 153-156 (1975).

Kumar, et al.; "Spinal cord stimulation for chronic pain in peripheral neuropathy," *Surg Neurol* 46: 363-369 (1996).

Loubser and Donovan, "Diagnostic spinal anaesthesia in chronic spinal cord injury pain," *Paraplegia* 29: 25-36 (1991).

Magarinos-Ascone, et al., "High-frequency stimulation of the subthalamic nucleus silences subthalamic neurons: A possible cellular mechanism in Parkinson's disease," *Neuroscience* 115(4): 1109-1117 (2002).

Mills, et al., "Changes in metabotropic glutamate receptor expression following spinal cord injury," *Exp. Neurol.* 170: 244-257 (2001).

Simpson, "Spinal cord stimulation," *Brit J Neurosurg* 11(1): 5-11 (1997).

Sjolund, "Pain and rehabilitation after spinal cord injury: the case of sensory spasticity?," *Brain Res Rev* 40: 250-6 (2002).

Starr, et al., "Deep brain stimulation for movement disorders," *Neurosurg. Clin. N. Am.* 9(2): 381-402 (1998).

* cited by examiner

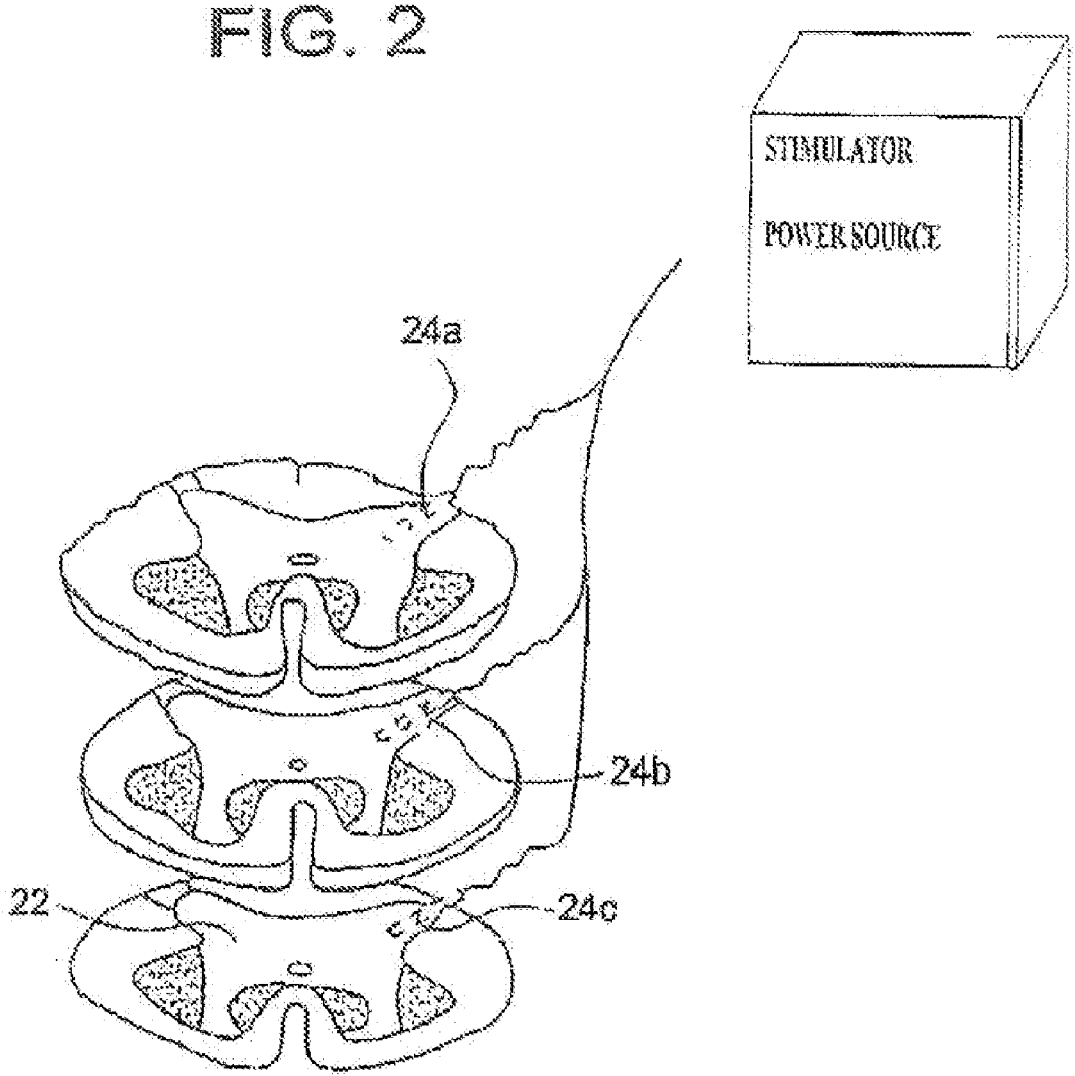

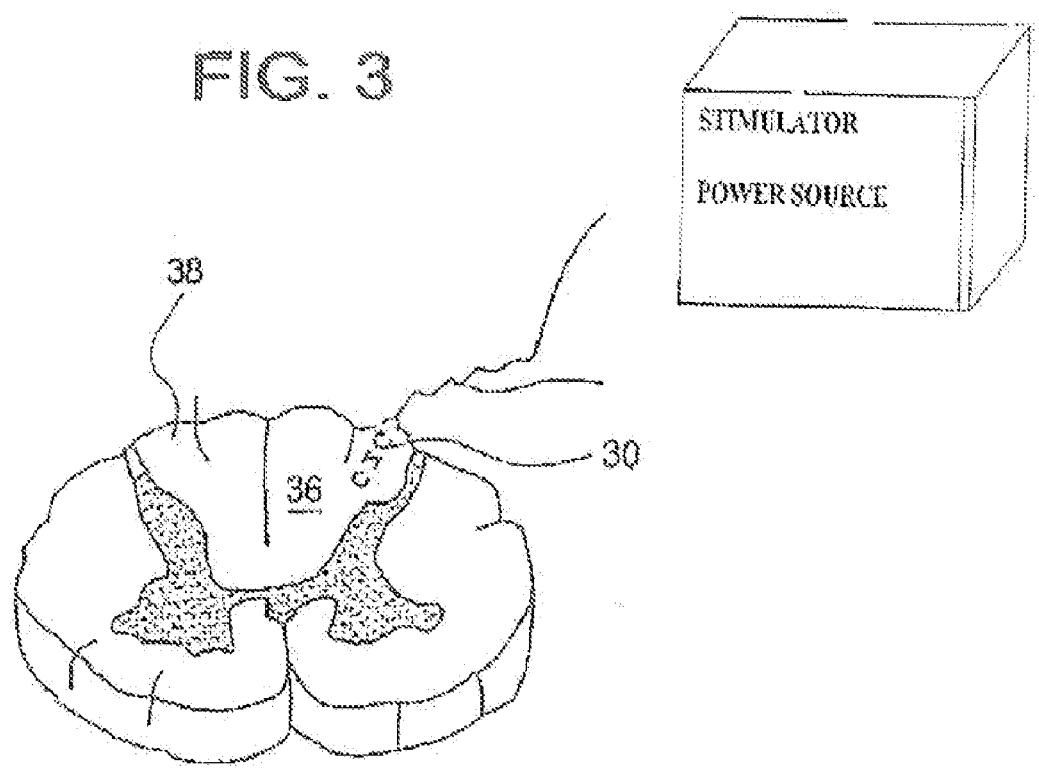

TREATMENT OF PAIN

CROSS-REFERENCE TO RELATED APPLICATIONS

This application claims priority to U.S. Ser. No. 60/488,857 filed Jul. 18, 2003.

FIELD OF THE INVENTION

This invention is generally in the field of compositions and methods for electrically stimulating the dorsal horn and other regions of the spinal cord to interfere with or otherwise block transmission of neural signals concerned with pain. The technique involves placement of electrodes directly into the spinal cord in order to activate selectively the target region. This technique improves delivery of electrical stimuli to the desired portion of the spinal cord and serves to decrease power requirements.

BACKGROUND OF THE INVENTION

Spinal Cord Injury. Pain resulting from trauma or other diseases of the nervous system is termed neuropathic pain. The abnormal pain includes ongoing (spontaneous or stimulus independent pain) and heightened pain to stimuli (hyperalgesia). Spinal cord injury (SCI), one cause of neuropathic pain, can result from a variety of causes including (among others) trauma, tumor, infection, congenital malformations, multiple sclerosis, and vascular lesions. Pain after SCI is a frequent occurrence. The development of pain can have devastating effects on the patients and even be of greater concern than the coincident loss of neurological function (paralysis). An important factor in the pathogenesis of SCI pain is the development of hyperexcitable cells near the site of injury (Christensen et al, *J Neurotrauma* 1997; 14:517-37). This hyperexcitability occurs in cells, activity in which is ordinarily concerned with pain. The abnormal spontaneous discharge leads to ongoing pain and accounts also for heightened pain (hyperalgesia) to natural stimuli (touch, heat, cold) at the border zone of the SCI. Patients feel pain at the level of spinal injury ("at level pain") and at regions below the injury ("below level pain"). The distal pain is typically stimulus independent and in a sense represents a "phantom" pain, since the patient may have no feeling in this area. There are many factors that cause this change in neuronal excitability at the region of injury. One factor could include changes in receptor expression in neurons in the dorsal horn (Mills et al, *Exp. Neurol.* 2001; 170:244-257; Chen et al, Neuroscience 2002; 111:761-773; Eide et. al, *J Neurol Neurosurg Psychiatry* 1996; 60:411-415.)

Numerous therapies have been attempted to treat SCI pain. Drug trials even with high doses of opioids are generally ineffective. (Burcheil and Hsu, *Spine* 2001 26:S161; Sjolund, *Brain Res Rev* 2002 40:250-6). Antidepressant, and anticonvulsant medications are also ineffective. Interventional approaches have largely proved ineffective as well. These have included neuro-destructive procedures, implantation of drug pumps into the lumbar intrathecal space, and various forms of electrical stimulation of the nervous system. For example, clinicians have tried implantation of catheters into the spinal fluid for purposes of targeted drug delivery. Though different drugs have been implanted, the results have proven disappointing.

Neuro-destructive procedures have been largely unsuccessful (Sjolund, *Brain Res Rev* 2002 40:250-6). Some clinicians have advocated lesions of the dorsal root entry zone in the region of SCI (DREZ operation), but whether this surgery is successful is controversial. It has been suggested that the success rates can be improved if dorsal horn recordings are used. (Falci et al. *J Neurosurg* 2002, 97(2 Suppl):193-200). However this approach contributes to the damaged state and pain may recur or even become worse in the long term. In any case further spinal cord destruction leads to further permanent loss of spinal cord function and therefore is an unsavory choice for a patient with SCI (Denkers et al, *Spine* 2002 27:E177-84; Sjolund, *Brain Res Rev* 2002 40:250-6; Burcheil and Hsu, *Spine* 2001 26:S161).

Electrical stimulation of the spinal cord with electrodes placed in the epidural space (or within the dura) is commonly used to treat a variety of pain problems. It has been scientifically tested and approved by the United States Food and Drug Administration (FDA) as a safe and effective treatment for certain types of chronic pain associated with the trunk and/or limbs. This technique, sometimes termed dorsal column stimulation (but distinct from the present invention which involves intramedullary spinal cord stimulation in the dorsal horn and other spinal cord structures), has proven ineffective for pain from SCI (Kumar et al; *Surg Neurol* 1996; 46:363-369). Subdural spinal stimulation has also been tried as a technique to stimulate the surface of the spinal cord (Hunt et al 1975 *Surg Neurol* 4:153-156), but this technique became obsolete with the development of better epidural electrodes.

There remains a need for better pain control in patients with chronic pain.

It is therefore an object of the present invention to provide a device and methods for use thereof for alleviation of chronic pain.

SUMMARY OF THE INVENTION

Electrodes placed directly into the spinal cord (in contradistinction to surface stimulation as is provided by epidural stimulation) are used to provide spinal cord stimulation for pain control. Electrodes are placed directly into the dorsal horn, dorsal column, spinothalamic tract, nucleus cuneatus, nucleus gracilis, spinal tract of V, or spinal nucleus of V (nucleus caudalis) depending on the source of pain. This "intramedullary" stimulation "jams" or otherwise prevents the pain signal from being transmitted. The placement of the electrodes is accomplished through an open surgical procedure in which the dura is opened to allow the surgeon direct access to the spinal cord. In the case of SCI (or disease), the electrodes are positioned in the dorsal horn of the spinal cord within several dermatomal segments of the lesioned site. Direct stimulation of the dorsal horn should be effective to relieve pain arising from diseases and/or injury of the peripheral nervous system as well, and thus represents an alternative to dorsal column stimulation with epidural electrodes. Stimulation with intramedullary electrodes may be used to treat other types of pain where stable stimulation of the dorsal columns (and the analogous structures for the face), or their nuclear counterparts (nucleus cuneatus, nucleus gracilis, nucleus caudalis) should relieve pain. Stimulation of the spinothalamic tract may also be achieved by intramedullary placement of electrodes. The method provides a means to stimulate the targeted area directly, creating a stable means of stimulating the desired area, and decreasing stimulation of other structures.

Each intramedullary electrode lead may be composed of one of more contact points. There may be one or more electrodes. The multiple leads and contact points provide a number of potential stimulus permutations. The ideal stimulus configuration can be determined after electrode implantation. The electrodes can be stably anchored in the spinal cord dorsal horn to prevent electrode migration. The electrodes are positioned in the spinal cord with electrode leads of sufficient length to prevent movement of the electrode from its fixed position during movements of the neck and torso. In some cases affixing the electrodes to the dentate ligament or dura or other extradural structures may be of use to prevent further the problem of electrode migration.

BRIEF DESCRIPTION OF DRAWINGS

FIG. 2 is a perspective drawing showing that one or more electrodes are placed into the dorsal horn immediately adjacent to the region of SCI. Multiple contacts permit various stimulation paradigms to be employed to maximize effectiveness and minimize untoward side effects. In cases of bilateral pain, the electrodes are placed bilaterally.

FIG. 3 is a perspective drawing showing electrodes placed into the portion of the dorsal column that serves the painful region. If pain is bilateral the electrodes are placed bilaterally.

DETAILED DESCRIPTION OF THE INVENTION

I. Devices

A. Electrodes

Figure 1:
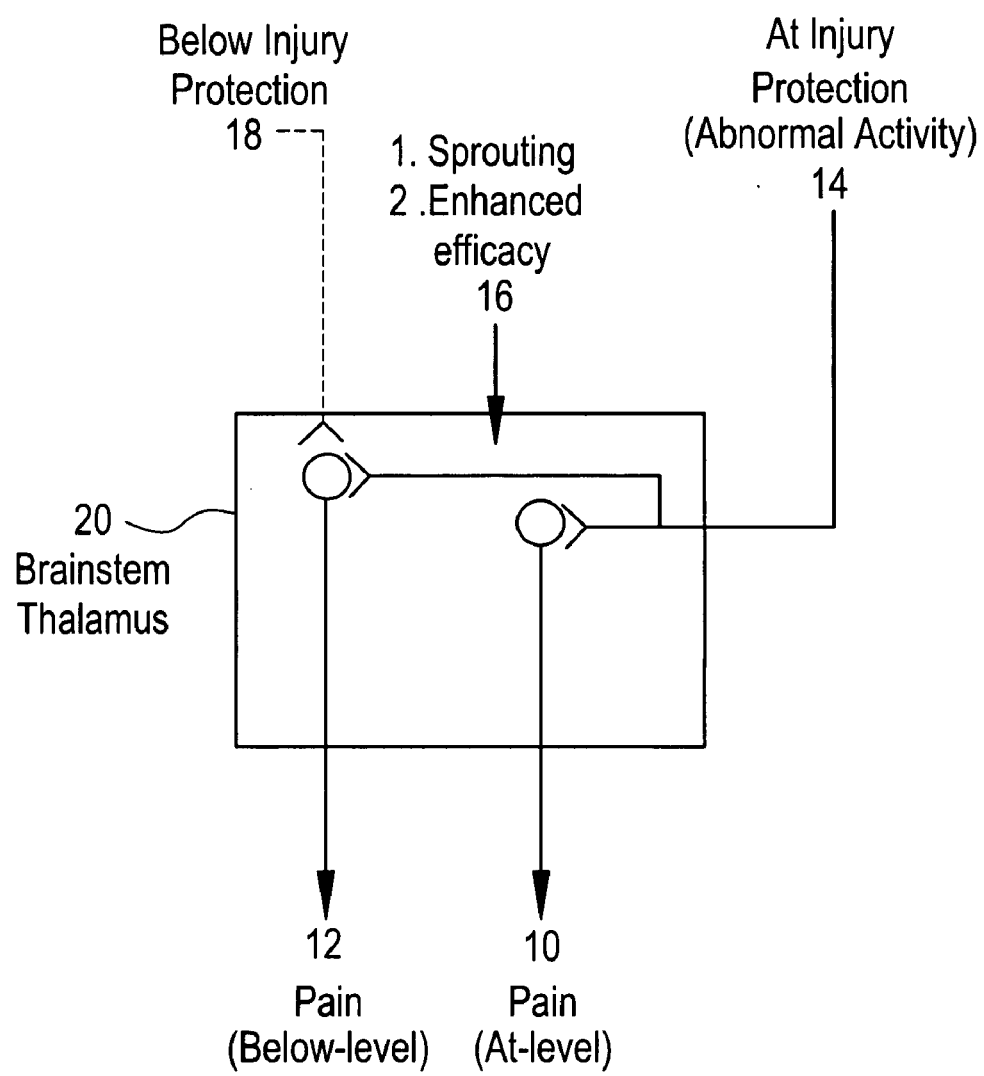
FIG. 1 is a schematic of how the dorsal horn in the region of SCI develops the capacity to signal pain in body regions at and below the level of SCI. Data indicate that increased discharges occur in the dorsal horn area subjacent to the site of SCI (e.g., Falci S, Best L, Bayles R, Lammertse D, Starnes C. J Neurosurg. 2002 September;97(2 Suppl):193-200. Dorsal root entry zone microcoagulation for SCI-related central pain: operative intramedullary electrophysiological guidance and clinical outcome). Cells in the thalamus that have lost inputs from distal regions (as a result of the SCI) recruit inputs from the abnormal dorsal horn cells near the SCI. Thus, the inputs from this spinal cord region acquire the capacity to signal pain in the distal regions of the body. The electrodes provide a means to block the inputs from these abnormal cells to the brain and thus control pain felt by the patient at and below the level of SCI.

Electrodes can be obtained from a variety of commercial sources. These are typically characterized by small size and flexibility.

Flexible electrodes are described by U.S. Pat. Nos. 6,024,702 and 5,012,810 incorporated by reference herein. Flexible conductive materials can also be used in making the electrodes as described in U.S. Pat. No. 6,495,020. For example, an electrode member can comprise a strip of material having a thickness of about 10-20 micrometers, such as IMPERIAL® lapping film No. 15 MIC LF S/C (3M Co®, St. Paul, Minn.), having a coating of silver/silver chloride of about 0.3-0.7, and preferably about 0.5, micrometers thick thereon.

The electrodes must be small enough to be implanted into the dorsal horn and other areas of the spinal cord. One such device is, for example, the MEDTRONIC® Model 3387 quadripolar lead, which has been approved by the FDA for several years for unilateral deep brain stimulation for treating tremor. There are four platinum-iridium contacts that are 1.5 mm in length and separated by 1.5 mm. Stimulus parameters such as amplitude, duration, and frequency can all be adjusted externally.

In a preferred embodiment, multi-contact electrodes are used with an array placed in a target area. The electrode leads are several millimeters in length with open contacts along the electrode. These electrodes are very similar to the deep brain stimulation electrodes that have open contacts. Each contact can be post-hoc programmed to be anodal or cathodal. For example, if three separate electrodes are implanted into the spinal cord, and each electrode has three open contacts, it is possible to program many thousands of potential combinations (each electrode may be anodal, cathodal, or inactive). One or more electrodes are placed into the spinal cord in the appropriate position (e.g., in the dorsal horn immediately adjacent and rostral to the region of SCI). Multiple contacts permit various stimulation paradigms to be employed to maximize effectiveness and minimize untoward side effects. In cases of bilateral pain, the electrodes are placed bilaterally.

B. Stimulators

Spinal cord and brain stimulators represent a large group of electrical stimulators that are implanted for a wide variety of indications. Existing spinal and brain stimulators can affect dorsal roots, dorsal columns, and other sites within the brain. The technical and surgical aspects have been reviewed by Simpson (*Brit J Neurosurg* 1997; 11:5-11).

The method is designed to work with existing spinal cord and brain stimulation devices. These stimulators typically consist of three components: the power source, an implanted receiver, and electrodes. An external controller allows the device to be custom programmed to idealize the electrical stimulation parameters. Stimulators delivering charge-balanced pulses, either by constant-current or constant-voltage, are preferred. These devices can also be either microprocessor-controlled impedance-sensitive pulse generators, or piezo-electric current devices.

Appropriate stimulators and electrodes for this method include, but are not limited to, those made by MEDTRONICS® (Minneapolis, Minn.) and ADVANCED NEUROMODULATION SYSTEMS, INC® (Plano, Tex.), NEUROMED® (Ft. Lauderdale, Fla.) and EXONIX™ (Miami, Fla.). Examples of these are described in U.S. Pat. Nos. 4,044,774, 5,501,703, 6,027,456, 6,314,325 and PCT application WO 99/56818.

II. Methods of Use

A. Patients to be Treated

1. Spinal Cord Injury. Pain occurs frequently as a complication of SCI. SCI may result from congenital anomalies (e.g., syringomyelia), tumor, trauma, infection, disc herniation, degenerative disease (e.g., spinal stenosis), vascular disease, and demyelinating diseases (multiple sclerosis), and other autoimmune disorders. The damaged site is also called a lesion. Patients describe pain in areas that have lost afferent input to the brain as well as at the border zone of the spinal cord lesion. The pain can vary in intensity, frequency of episodes, duration of episodes, and quality of pain experienced.

Chronic pain problems can occur in individuals with neurologically complete or incomplete injuries. Two types of pain may develop after SCI: 1) segmentally distributed pain ("at level pain"), and 2) pain in the body below the lesion ("below level pain"). In cases of complete spinal cord lesions this second type of pain by definition is stimulus-independent.

2. Other pain conditions affecting the arms and legs. Dorsal column stimulation is accomplished currently with electrodes placed into the epidural space. This technique is useful for treatment of many pain conditions, including lumbar radiculopathy. A requirement for this technology to work is that there has to be "coverage." This means that the patient must feel paresthesias in the area felt to be painful. Electrodes must be positioned precisely to achieve this coverage. In certain instances coverage is difficult or impossible to obtain. One reason for this problem is that electrodes may migrate with spinal movements. The problem is especially apparent in regards to spinal cord stimulation for treatment of neck and upper extremity pain conditions. Neck motion changes the contact with the epidural space such that in one position the stimulation may be too strong, and in another the stimulation may be too weak. The result is that clinical efficacy is lost. Even if the electrodes are fixed to the dura, the spinal cord distance from the dura also varies with bodily movement. This leads to variations in delivery of electrical stimulation of the spinal cord.

These problems are overcome by placing the electrodes directly into the dorsal columns or their nuclear equivalents (nuclei cuneatus and gracilis). Evoked potential measurements help establish the ideal locations for electrode placement in patients that are under general anesthesia for the surgery required to place the electrodes.

3. Facial pain. The pain processing pathways for the face involve the nucleus caudalis and descending tract of V, both located in the upper part of the cervical spinal cord. Patients with facial pain can not be treated with conventional "dorsal column" epidural stimulation because these targets are not accessible. The electrodes can be implanted directly into the pain processing pathways for the face in the upper cervical spinal cord. This provides a direct means of stimulating the appropriate target without over stimulating other targets. Evoked potential monitoring can provide a physiological means intraoperatively to guide placement of the electrodes into the appropriate target.

B. Targets for Electrode Implantation

The method of treatment of pain involves: (a) targeting areas of the spinal cord that generate signals that lead to pain; and (b) ways to apply direct stimulation to the spinal cord of targets that are involved in pain inhibition (such as the dorsal columns) in situations where epidural activation of these targets is technically not feasible or is associated with untoward side effects.

1. Targeting the dorsal horn with electrical stimulation at the level of injury in cases of SCI.

Whereas stimulation of the dorsal columns (with epidural electrodes) has proved efficacious in treating a variety of pain disorders, this technique has failed to help with pain from SCI. A major region for this is that the region of the dorsal column that conducts signals from the painful region has been disconnected. Thus stimulation fails to provide coverage given that the appropriate targets have undergone Wallerian degeneration. It is clear that a radically different approach must be considered to treat pain from SCI.

The region responsible for initiating the neural signals responsible for pain must be rostral to the transection site of the spinal cord, since involvement of the brain is ultimately necessary to have pain, and because signals below the level of injury have no way of reaching the brain (18). One consideration is that the pain signals arise in the brain itself The following lines of evidence suggest that this conclusion is incorrect. (a) If the pain signals arise in the supraspinal region independent of the injured spinal cord then spinal anesthesia should have no effect on the pain. The opposite, however, is true. Loubser and Donovan (Loubser and Donovan; *Paraplegia.* 1991 January 29(1):25-36) noted that application of spinal anesthesia often relieved distal pain. Intrathecal lidocaine was delivered to paraplegic and quadriplegic patients in concentrations such that the highest effect of the anesthesia would be T4. In this blinded protocol, the anesthetic had a significant pain relieving effect. Thus, the pain signaling neurons must be in the region of the spinal cord transection. (b) Other investigators have found that spinal cord ablative procedures may correct pain from SCL Of particular interest is the finding that thermal destruction of the dorsal horn near the region of spinal injury may relieve pain in distal regions (Falci et al; *J Neurosurg* 2002 September; 97:193-200). This can be explained if the dorsal horn region at the level of SCI has developed the capacity to signal pain in the distal regions.

Dorsal horn neurons in the region of the SCI are known to become abnormally active (14). The dorsal horn is the primary relay center in the spinal cord for painful stimuli to the brain. The nociceptors synapse on neurons in the marginal zone, substantia gelatinosa and deeper layers and from these regions information ascends to the brain. Normally the spinothalamic tract transmits the nociceptive information with nerve fibers ascending in the contralateral ventrolateral spinal cord to the brainstem and ventroposterolateral thalamus.

Since these dorsal horn cells normally signal pain at the respective segmental level, it is clear that these cells likely generate the "at level" pain (10). In that the dorsal horn region just above the SCI may also still have connections with peripheral nerve inputs, this hyperexcitability also accounts for why hyperalgesia (including allodynia) is also present at the level of injury. The reasons why pain develops in distal body regions (viz., legs, feet, and sacral region) after spinal cord transection may be understood by considering two interrelated mechanisms: (1) abnormal spontaneous activity in pain generating neurons in the dorsal horn of the spinal cord at (and near) the level of injury (14); and (2) acquired capacity of these cells to activate neurons in the brainstem/thalamus/cortex that signal sensation in the body regions that have lost input to the brain as a result of the SCI (16).

FIG. 1 illustrates these concepts. The neurons in the dorsal horn near the area of injury develop abnormal spontaneous activity (14). This spontaneous activity accounts for the so called "at level" pain (10). Normally these neurons signal pain confined to their segmental inputs. The areas in the brain, such as the thalamus, that receive inputs from the spinal cord caudal to the region of SCI (18) demonstrate plasticity such that they now receive inputs from the cells of the dorsal horn at the level of injury (16). The inputs from the segmental dorsal horn neurons near the area of SCI acquire the capacity to activate the neurons that signal pain in the caudal areas of the body by way of synaptic sprouting and/or physiological changes in synaptic efficacy (16). This concept of SCI pain accounts for the findings of Falci et al (2002) that destruction of the dorsal horn near the transection site may eliminate "at level" as well as "below level" pain. Additionally this concept explains why spinal anesthesia may eliminate below level pain. For example, the T7 level of the dorsal horn provides pain and temperature sensation at the T7dermatome. If the cord is severed just below the T7 region, the T7 dorsal horn cells become hyperexcitable. Ordinarily these cells would simply signal pain at the T7 (mid-thoracic) regions. It is the border zone at the lesion site, or immediately proximal to the lesion, that is the site of aberrant neuronal activity (14). The abnormal activity in the dorsal horn cells is relayed not only to the regions in the thalamus that normally receive the T7 input but also regions of the thalamus that ordinarily serve the distal regions. This rearrangement (from sprouting and/or changes in synaptic efficacy) in the thalamus occurs because the thalamic area that serves the distal region has been denervated (20). The changes might also occur in other areas such as the cortex. Thus the abnormal activity at T7 leads to abnormal pain at in the T7 dermatome but also the regions distal to the SCI.

Given that the culprit in SCI pain is the dorsal horn, a potential therapy is to block that abnormal neural activity in the dorsal horn. This might be achieved by lesioning the dorsal horn as advocated by Falci et al (2002). The disadvantages of this approach are that this technique extends the level of SCI, is irreversible, and potentially establishes a new zone of SCI that could create new sources of pain. Stimulation of the generator site in the dorsal horn provides a non-destructive means of blocking the pain signaling.

In the field of movement disorders, (e.g., Parkinson's disease) certain brain targets can be stimulated at high frequency (>100 Hz) with an implanted microstimulator and achieve a therapeutic effect (Starr et al *Neurosurg. Clin. N. Am.* (1998) 9(2):381-402). It is important to note that the targets for stimulation are the same as the targets for ablation. As described herein, the target for stimulation (dorsal horn) is also the same as the target for lesioning in treatment of pain from SCI. Although not critical to the method of treatment, possible mechanisms that would account for how stimulation relieves pain include: (1) activation of nearby inhibitory cells, and (2) a jamming mechanism in which the rate of stimulation leads to loss of conductive capacity in the neurons (Magarinos-Ascone C, Pazo J H, Macadar O, Buno W. Neuroscience. 2002;115(4): 1109-17 High-frequency stimulation of the subthalamic nucleus silences subthalamic neurons: a possible cellular mechanism in Parkinson's disease; Beurrier C, Bioulac B, Audin J, Hammond C.); J Neurophysiol. 2001 April;85(4): 1351-6. High-frequency stimulation produces a transient blockade of voltage-gated currents in subthalamic neurons); (3) an alteration of the pattern of discharge such that the rostrally conducted impulses no longer activate brain areas concerned with pain signalling. Thus, implantation of an electrode and stimulation offers an alternative to ablation and avoids destruction of spinal cord tissue. This reversible intervention can be removed or stop being used at a later time if other therapies emerge. The stimulation parameters can also be adjusted so that the therapy can be graded to a certain level as opposed to the all-or-none action of surgical ablation. Multiple implant sites can be used and post-hoc programming can be used to determine the ideal electrode configuration.

2. Technique for Dorsal Horn Stimulation.

Dorsal horn stimulation preserves the hyperexcitable neurons at the level of the lesion while inactivating their function or capacity to transmit signals to the brain. As shown in FIG. 2, the electrodes (24) are inserted into the gray matter of the spinal cord, preferably at the level of the lesion (22). Since the border zone is the target site for dorsal horn stimulation, it is most preferable that the electrodes (24*a*, 24*b*, 24*c*) be positioned at and within 2-3 spinal segments rostral to the lesion (22). Placement of the electrodes must be done precisely and requires surgical exposure of the dorsal horn through a laminectomy. Anatomical landmarks are used to guide placement of the electrodes. It is possible that electrophysiological monitoring can be used as well to guide placement as described by Falci et al (2002). Programming of the electrical stimulation paradigm postoperatively with the patient awake will determine the ideal configuration of stimulation. The variety of electrode placements intraoperatively allows the best electrical stimulation paradigm to be used in order to maximize pain relief and minimize side effects.

3. Use of Intramedullary Electrodes to Stimulate Targets in the Spinal Cord Other than the Dorsal Horn.

Spinal cord stimulation is a frequent therapeutic tool to treat a variety of pain states. Electrodes are placed into the epidural space and positioned so that the patient feels parethesias in the region of pain. The patient indicates whether there is pain relief and the decision is made to do a permanent implant. Electrodes have been placed in the subdural space and intradural compartment, but because of ease of use epidural stimulation is the prevailing technique presently utilized. This technique, though effective, suffers from problems with obtaining stable stimulation. The electrodes may move or the electrical connectivity with the desired target may be such that excessive stimulation has to be applied to unwanted regions of the spinal cord in order to stimulate the desired target (Barolat *Arch Med Res* 2000 31:258-262; Holsheimer et, al., *Neurosurg* 1998 42:541-547). While somewhat a problem for the lower extremities, this problem with inadequate stimulation of the desired targets in the dorsal column is especially limiting for the upper extremities. Neck motion changes the conduction properties in patients such that the patient experiences sags and surges in the intensity of the stimulation with normal neck motion. Several attempts have been tried to circumvent these technical problems. For example, suturing of the electrode to the adjacent soft tissue or bone is one method. Another method provides a lead anchor (LA) and/or suture sleeve (SS) that may be used after insertion of the electrode array into the spinal canal in order to secure and maintain the position of the electrode and prevent its dislodgement due to axial loads that are placed upon the lead (described in U.S. Pat. No. 6,516,227). A paddle lead has also been used with a variety of electrode contact configurations or arrays so that a combination can be used if the first stimulus combination becomes inactive (U.S. Pat. No. 6,308,103). These techniques are still insufficient because other factors affect the stimulation efficacy. The conduction to the dorsal columns is also affected by the distance between the dura and the spinal cord. It is well known that with different head position or trunk positions that the space between the dura and the spinal cord varies. This is a further factor that gives rise to sags and surges in the stimulation afforded by durally based electrodes.

Therefore, the method described herein involves placement of intramedullary electrodes into the desired target. Intramedullary refers to the substance of the spinal cord.

Potential targets include the dorsal columns, the nucleus cuneatus (arm), nucleus gracilis (leg and sacral regions), nucleus caudalis and spinal tract of V (face and neck), and the spinal-thalamic tract. The dorsal horn may also be included as a target for stimulation in cases other than SCI. As shown in FIG. 3, electrodes (30) can be inserted directly into the spinal cord white matter (36) comprising the dorsal column projection pathway. The lead (34) is connected to a stimulator. The cuneate fascicle (38) is one of the nerve pathways relaying sensory information from the spinal cord to the brain. This provides more stable stimulation.

Fibers in the dorsal column pathway normally relay touch and position sense information and ascend to the medulla where they synapse onto neurons in the nucleus cuneatus and nucleus gracilis. Neurons in these two nuclei project along the medical lemniscus and synapse on cells in the ventroposterolateral (VPL) thalamus. The VPL thalamus is the central receiving area for sensory information before transmission to the cortex.

The position of cathodes and anodes, and configuration of the stimulation are the major determinants of whether the patient will experience "coverage." Coverage refers to the desired goal of having the patient feel paresthesias in the painful area in the case of dorsal column stimulation (including here stimulation of nuclear areas, nuclues cuneatus, and nucleus gracilis).

Stimulation of the nuclues cuneatus and nucleus gracilis provides a way to obtain results similar to dorsal column stimulation. These nuclei receive inputs from the dorsal columns. In particular, stimulation in these areas would be expected to provide widespread coverage with less power requirements if the patient has widespread pain.

A further use of the intramedullary spinal cord stimulating electrodes is to stimulate the nucleus caudalis and spinal trigeminal tract. These structures are immediately lateral to the cuneate fasciculus below the level of the medulla, and are the facial analogs of the dorsal horn. Implantation of electrodes in these structures should relieve facial pain in a similar fashion to how pain is relieved by dorsal horn stimulation.

Stimulation with implanted electrodes for treatment of facial pain is presently unsatisfactory. The dorsal column equivalent for the face region is sufficiently far from the epidural space that epidural electrodes would not be expected to provide selective stimulation of the relevant target. Recently neurosurgeons working with implantation of epidural electrodes over motor cortex observed some promising results. There are potential liabilities for stimulation of the cortex of the brain, however, including the possibility, for example, of inducing epilepsy. Moreover, the mechanism by which motor cortex stimulation works is unknown. The types of patients helped with this technique may be completely different from the patients who should derive benefit from intramedullary stimulation of the spinal cord.

C. Electrode Implantation

The electrodes are inserted by the surgeon directly into the spinal cord tissue with direct visual control. Electrophysiological recordings may be made as well to ensure that the electrode positioning is accurate. Typically, the leads are implanted in a procedure called a bilateral laminectomy. This procedure is considered major surgery and entails removing two or three spinous processes and one or more full set of lamina. The dura is opened and the surgeon visualizes the spinal cord directly. The anatomic target is selected and the electrodes are placed (this may require use of the operating microscope).

The electrodes will be placed directly by the surgeon into the appropriate region of the spinal cord. The surgeon can be aided by electrophysiological data. The nerve that serves the painful area can be stimulated intraoperatively and the evoked potentials associated with this stimulation can be used to place the electrodes into the ideal regions of the dorsal columns as well as other targets. Such methods are known in the art and are described in U.S. Pat. No. 6,027,456. Electrophysiological recordings are used in cases of SCI to guide spinal cord lesioning (Falci, 2002). Similar guidance should be useful for electrode positioning.

In a preferred embodiment, the electrodes are implanted at and just above the SCI site in the dorsal horn. Recent advances in electrode arrays with multiple contacts have allowed for optimal combinations of contacts to be stimulated after implantation.

D. Connection to and Use of the Stimulator

The stimulator is hermetically sealed from the external environment except for the electrode leads and is sterile packaged to minimize potential for infection after implantation. The electrodes may be connected to existing stimulator systems in one of two ways. One version consists of an external (to the body) radio frequency transmitter and antenna, with an implanted radiofrequency receiver and stimulation leads. In an alternative version the transmitter is implanted and thus an external antenna is not needed.

The electrodes are connected to an implanted receiver via conductive leads. The stimulation at a range of potential frequencies and voltages is provided in similar fashion as what is provided with conventional dorsal column and deep brain stimulation devices. Multiple contacts permit various stimulation paradigms to be employed to maximize effectiveness and untoward side effects. In cases of bilateral pain, the electrodes are placed bilaterally. The dorsal horn stimulation will lead to relief of pain.

The intensity of the stimulation must be in an amount effective to provide coverage of the areas where the patient describes feeling pain. For example, if the patient is experiencing pain in the right arm, but stimulation evokes sensation in the right leg, coverage is not adequate. Paresthesia coverage can be altered by proper positioning of the anodes and cathodes and by programming the electrical stimulation configuration. In a preferred embodiment, multiple electrode leads and contacts permit a "stimulation array" wherein effective coverage is obtained to relieve pain by stimulating different contacts.

Stimulus parameters can be adjusted to manipulate the strength, duration and frequency of stimulation. The parameters (electrode or electrodes used, number of pulses, amplitude, pulse to pulse interval, duration of pulses, etc.) of the stimulation may be set or varied as a result of the detection of signals from the patient's body including the nervous system or set by a physician. Typical stimulus parameters include pulse duration between 60-120 microseconds, pulse amplitude between 0.1-7V, and stimulus frequency between 10-300 Hz. Observations in the treatment of movement disorders have shown that on a behavioral level, a stimulation of >100 Hz gives the same results as lesioning the area (Starr et al. 1998 *Neurosurg Clin N Am* 9(2):381-402).

A stimulation regimen can be determined empirically to give a certain amount of "on time," and "off time" to give optimal balance between analgesia, prolonged battery life and patient satisfaction. An external programming device can be used to adjust all stimulus parameters and also determine which electrodes are activated, and furthermore which electrodes serve as cathodes and anodes.

In summary, the method typically includes the steps of implanting the electrodes, attaching the electrode leads to the receiver and power source and applying a stimulus in an effective amount to decrease pain due to the disease or injury. In one embodiment, different electrodes are positioned rostral to, and at the level of spinal cord disease or injury. In another embodiment, the electrodes are positioned in the dorsal column, to treat pain from the neck down. In still another embodiment, the electrodes are positioned in the nucleus cuneatus for treatment of pain in the arm. In additional embodiments, the electrodes are positioned in the nucleus gracilis for treatment of pain in the leg and sacral regions or in the nucleus caudalis and spinal tract of V for treatment of pain in the face and neck. In other embodiments, the electrodes are positioned in the spinal-thalamic tract or into the spinothalamic tract to treat pain in the contralateral arm, trunk, leg, or sacral area. In yet another embodiment, the electrodes are positioned in the dorsal horn of the spinal cord within several dermatomal segments of the lesion site.

In the preferred method, the electrodes directly stimulate the dorsal horn in an amount effective to relieve pain, usually by a pulse duration between 60 and 120 microseconds, a pulse amplitude up to 7 volts, and a stimulation frequency greater than 20 Hz.

There are drawbacks to caring for a chronically implanted device, but these are known in the art. There is always the risk of infection and migration of the electrodes with any implanted foreign object. If a power supply is worn externally and if batteries are used, they must be changed regularly. A single stimulator may also be limited to a particular effective field. Operative risks including spinal cord injury are associated with implantation of the electrodes. Despite these drawbacks, intramedullary stimulation may provide pain relief where other alternatives are ineffective.

Modifications and variations of the present invention will be obvious to those skilled in the art from the foregoing detailed description. Such modifications and variations are intended to come within the scope of the following claims.

I claim:

1. A system for treating pain comprising
electrodes configured to be fixated within the spinal cord dorsal horn, the electrodes comprising electrode leads of sufficient length to prevent movement of the electrodes from their fixed position during movements of the neck and torso,
a receiver coupling the electrodes to an external or internal power source, and
a power source for applying stimulation to the spinal cord dorsal horn where the electrodes are fixed.

2. The system of claim 1 comprising a specialized stimulation array comprising multiple separate electrode leads each with multiple contact points.

3. The system of claim 2 wherein the stimulation array can be activated in an effective amount to provide relief from pain.

4. The system of claim 1 further comprising means for affixing the electrodes to the dentate ligament or dura or other extradural structures.

5. The system of claim 1 wherein the electrodes are flexible.

6. A method for treatment of pain associated with CNS disease or injury comprising implanting one or more electrodes within the spinal cord dorsal horn at or adjacent to the site of disease or injury, wherein the electrodes are configured to be fixated within the spinal cord dorsal horn, the electrodes comprising electrode leads of sufficient length to prevent movement of the electrodes from their fixed position during movements of the neck and torso.

7. The method of claim 6 further comprising providing
a receiver coupling the electrodes to an external or internal power source, and
a power source for applying stimulation to the spinal cord dorsal horn where the electrodes are fixed.

8. The method of claim 7 further comprising attaching the electrode leads to the receiver and power source and applying a stimulus in an effective amount to decrease pain due to the disease or injury.

9. The method of claim 7 wherein the electrodes directly stimulate the dorsal horn in an amount effective to relieve pain.

10. The method of claim 9 wherein the region of implantation is stimulated with a pulse duration between 60 and 120 microseconds, a pulse amplitude up to 7 volts, and a stimulation frequency greater than 20 Hz.

11. The method of claim 6 wherein different electrodes are positioned rostral to, and at the level of spinal cord disease or injury.

12. The method of claim 6 wherein the electrodes are positioned in the dorsal column, to treat pain from the neck down.

13. The method of claim 6 wherein the electrodes are positioned in the nucleus cuneatus for treatment of pain in the arm.

14. The method of claim 6 wherein the electrodes are positioned in the nucleus gracilis for treatment of pain in the leg and sacral regions.

15. The method of claim 6 wherein the electrodes are positioned in the nucleus caudalis and spinal tract of V for treatment of pain in the face and neck.

16. The method of claim 6 wherein the electrodes arc positioned in the spinal-thalamic tract.

17. The method of claim 6 wherein the electrodes are placed into the spinothalamic tract to treat pain in the contralateral arm, trunk, leg, or sacral area.

18. The method of claim 6 wherein the electrodes are positioned within the dorsal horn of the spinal cord within several dermatomal segments of the site of disease or injury.

19. The method of claim 6 wherein the electrodes are stably anchored to prevent electrode migration.

* * * * *